(12) United States Patent
Rassman et al.

(10) Patent No.: US 8,941,727 B2
(45) Date of Patent: Jan. 27, 2015

(54) APPARATUS AND METHOD FOR MAPPED HAIR METRIC

(75) Inventors: William Rassman, Studio City, CA (US); Jae P. Pak, Torrance, CA (US)

(73) Assignee: William Rassman, Los Angeles, CA (US)

( * ) Notice: Subject to any disclaimer, the term of this patent is extended or adjusted under 35 U.S.C. 154(b) by 187 days.

(21) Appl. No.: 13/372,405

(22) Filed: Feb. 13, 2012

(65) Prior Publication Data

US 2012/0148127 A1  Jun. 14, 2012

Related U.S. Application Data

(62) Division of application No. 11/682,763, filed on Mar. 6, 2007, now Pat. No. 8,115,807.

(51) Int. Cl.
*A61B 1/00* (2006.01)
*G06K 9/00* (2006.01)
*A61B 5/107* (2006.01)
*A61B 5/00* (2006.01)

(52) U.S. Cl.
CPC ............... *A61B 5/1072* (2013.01); *A61B 5/448* (2013.01)
USPC .............................................. 348/77; 382/128

(58) Field of Classification Search
CPC ........ A61B 5/448; A61B 5/1072; G01B 3/18; G01B 3/205; G01B 5/08
See application file for complete search history.

(56) References Cited

U.S. PATENT DOCUMENTS

| | | | | |
|---|---|---|---|---|
| 5,331,472 A | * | 7/1994 | Rassman | 359/894 |
| 6,389,150 B1 | * | 5/2002 | Amornsiripanitch | 382/100 |
| 2002/0090123 A1 | * | 7/2002 | Bazin | 382/128 |
| 2004/0201694 A1 | * | 10/2004 | Gartstein et al. | 348/207.99 |
| 2005/0181470 A1 | * | 8/2005 | Bova | 435/40.5 |
| 2005/0229418 A1 | * | 10/2005 | Cohen | 33/512 |
| 2006/0005409 A1 | * | 1/2006 | Cohen | 33/512 |

* cited by examiner

*Primary Examiner* — Peling Shaw
(74) *Attorney, Agent, or Firm* — Lawrence S. Cohen

(57) ABSTRACT

Apparatus for determining the status of hair bulk in an area of a scalp is operative to provide a metric over a sufficiently large area to permit revisiting with only negligible misalignment error. Accurate re-measurement of hair status in accurately identified areas produces a reliable metric for determining degree of hair loss and or the effectiveness of treatment.

8 Claims, 5 Drawing Sheets

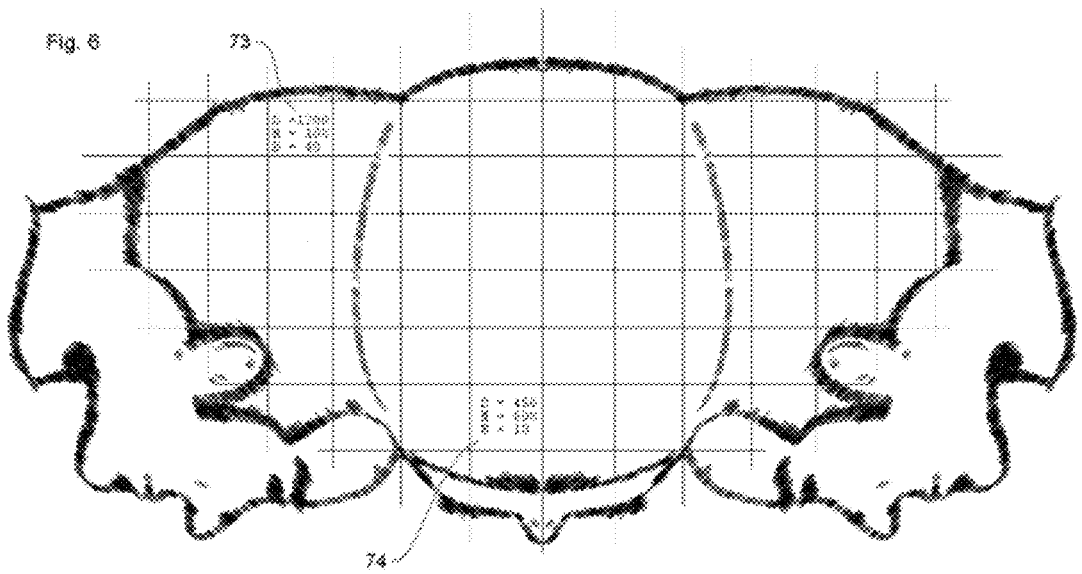
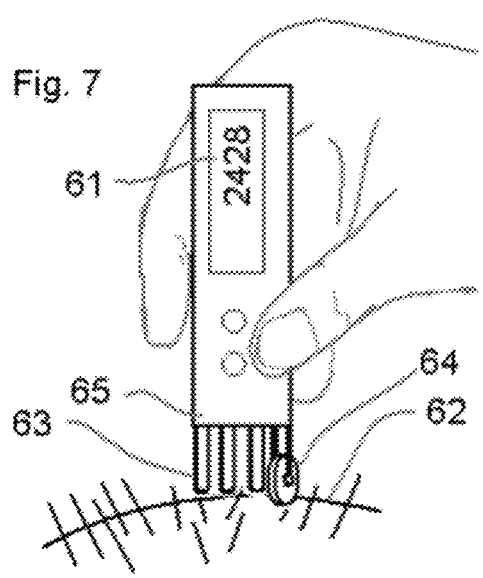

APPARATUS AND METHOD FOR MAPPED HAIR METRIC

This application is a divisional of U.S. application Ser. No. 11/682,763 filed on Mar. 6, 2007 the content of which is incorporated herein by reference and the priority of which is claimed.

RELATED APPLICATIONS

The present application is related to U.S. Pat. No. 5,331,472 issued Jul. 19, 1994 included by reference herein.

The present application is related to U.S. Pat. No. 6,253,771 issued Jul. 3, 2001 included by reference herein.

The present application is related to U.S. Pat. No. 4,807,163 issued Feb. 21, 1989 included by reference herein.

The present application is related to U.S. Pat. No. 7,098,910 issued Aug. 29, 2006 included by reference herein.

The present application is related to U.S. Pat. No. 7,006,657 issued Feb. 28, 2006 included by reference herein.

The present application is related to U.S. Pat. No. 6,993,851 issued Feb. 7, 2006 included by reference herein.

FIELD OF THE INVENTION

This invention relates to geographically mapping the characteristics of hair over a user defined areas of hair bearing skin and comparing the relative metrics between the aforementioned areas in four dimensions of time and space.

BACKGROUND OF THE INVENTION

Hair loss is a problem faced by many men and women. It is believed that the average person has about 100,000 hairs on their head and it generally takes greater than 50% of hair loss to notice a visual perceptional difference. While it is normal to lose about 100 hairs a day, it is nearly impossible to keep track of the rate and degree of hair loss during a given period of time by counting hairs. The measurement of hair bulk is one way to determine 'practical' changes in areas of the scalp or in the same area of the scalp over time.

There are three phases of a hair growth cycle and they are not all in the same phase at any one given time. Growth phase (Anagen phase) lasts anywhere from 2 to 6 years. This is the phase where hair is actively growing at approximately 10 cm per year. 85-90% of hair is at the anagen phase at any given time. Transitional phase (Catagen phase) lasts about 2 weeks. This is the phase where the hair follicles shrink and prepare to enter the resting phase. Resting phase (Telogen phase) lasts about 1-6 months. This is the phase where hair does not grow and generally falls out. Most hairs are shed in this phase, but at the end of the cycle, hair follicles re-enter the growth phase to start the cycle over again. At any given time approximately 10-15% of the scalp hairs are at the telogen phase and contribute no bulk value to the areas of hair baring skin while in the telogen phase.

The distinguishing factor which differentiates permanent scalp hair loss from cyclical hair loss is that the population of hair and the bulk of that hair decreases gradually in the affected areas. These changes in men impacted by genetic balding result in a permanent loss of hair bulk and a reduction of hair population (hair density).

The permanent loss of hair is often confined to limited anatomical sites. In men, hair loss generally follows a series of patterns (often referred to as "Male Pattern Baldness" or "Androgenic Alopecia" and are characterized by a generally agreed upon terminology called the "Norwood Classification of Hair Loss"). In women, it follows variable patterns which are more difficult to characterize. The process of losing hair also occurs at different rates, over different periods of time, and at different ages, even in the same individual. Hair loss in women can be diffuse without a pattern or they can be confined to areas of the front, top or crown of the head. In men, permanent hair is immune to the impact of genetic patterned hair loss and these areas are confined to the back and sides of the head.

As hairs become diseased, individual hairs may go through physical changes often referred to as miniaturization. Miniaturization is the process where a normal thickness hair shaft becomes thinner and thinner over time, often due to the genetically determined effects of aging and/or androgenic hormones on the terminal (normal) hair follicle. The process of miniaturization is generally a slow process in genetic balding. Hair shafts may lose 10% of their diameter, then 20%, then 30% and so on. Each degree of increased miniaturization reflects further progression of the genetic balding process, and produces a visually thinning look. This thinning look reflects a loss of hair populations and hair shaft thickness, and the thinning therefore is the results of loss of hair bulk (mass). A more limited segment of the population may just lose hair without going through the miniaturization process. Instruments that measure numbers of hairs and miniaturization exist as detailed in U.S. Pat. No. 5,331,472 issued Jul. 19, 1994 and these instruments are in wide use today.

The ability to diagnose hair loss in its earliest stages is dependent upon the early diagnosis of miniaturization, when it occurs. It is difficult to obtain a practical, accurate record of these measurements and the difficulties are compounded by many aesthetic factors such as the contrast between hair and skin color, hair thickness, hair character (wavy vs. straight vs. curly), and hair length. As an example, for the same amount of hair loss, there will be a more dramatic visual effect for someone with thin straight black hair on light skin than someone with thick wavy blond hair on light skin. Realistically, hair loss is a subjective observation and even with density measuring tools, estimating hair bulk loss is impractical and limited. Socially detectable hair loss is generally not evident until more than 50% of hair bulk has been lost and as a result, many men and women do not seek out expert help until they see obvious evidence of balding with bare scalp showing.

When a doctor views the scalp hair with high magnification, the degree of miniaturization and the location of the miniaturization are critical to establishing (1) the diagnosis and (2) the rate of the balding process which progresses over time. Because miniaturization is a relative measurement at any one time (comparing finer hair to the thickest hair), it takes substantial experience before this measurement can be useful to the individual clinician. Without good metrics, even the experienced physician exercises considerable subjectivity in the assessment. For repeated and accurate measurements, a tattoo must be placed at the exact point where the hair will be measured over time. Any place other than that exact point, will produce unreliable metrics that have limited value in establishing a hair metric. In our experience, from examining and following tens of thousands of patients with the Hair Densitometer (U.S. Pat. No. 5,331,472 issued Jul. 19, 1994), we have found that assessing the degree of miniaturization has useful predictive value when identifying the problems of genetic hair loss has commenced. Estimating the changes in hair bulk associated with hair loss and in particular hair loss over time, is near impossible. The amount of miniaturization in each section of the scalp gives the physician an ability to guess the extent (what areas are impacted) and the phasing of the hair loss (mild, moderate, severe hair loss) at that exact location and only at that exact location. In men who show more and more areas of miniaturization over time, the genetic balding can be considered active. In men treated with medications such as finasteride (Propecia), if the miniaturization of hair is reduced or the hair count is increased and if the areas under study are tattooed, it can be assumed that the balding process is responding to medical therapy at that exact location.

More often than not, the benefits when seen are observed because hair bulk returns more towards the original normal hair bulk as recorded in photographs or reported by the patient as his subjective view of the benefits of his/her treatment. Thus, quantitative measurement of hair count and estimates of hair shaft bulk (based upon miniaturization) in many hairs, which should become an essential tool for monitoring or diagnosing hair loss, turns out to produce inaccurate and non repeatable measurements.

Although there are numerous instruments and devices available for visually measuring hair count and hair shaft thickness at any particular point in the scalp, there exists no standardized method or automated process or device to process the data such that hair bulk assessments can be measured accurately for different section of the scalp, or for the same section of the scalp over different time periods. As the balding or miniaturization process occurs in patterns, the ability to estimate hair bulk today is extrapolated by counting and characterizing hair by hair counts in limited areas where the hair is cut short to measure it. Today's devices can count and measure individuals hairs at a particular location or the sum of individual hairs in a particular field of view. Hair by hair measurements are prone to human error due to its tedious nature and the subjectivity of human observation in analyzing an image and are rarely repeatable because the area under measurement are not exactly in the same area as previous measured.

SUMMARY OF THE INVENTION

Prior art systems are available for obtaining measurements of hair to determine the degree of hair loss in areas measured. U.S. Pat. Nos. 5,331,472 and 6,253,771 and 4,807,163 and 7,098,910 and 7,006,657 and 6,993,851 are examples of such systems. Commercial software packages are currently available (TrichoScan by a Germany company Tricholog, and Folliscope by a Korean company Hairscience) for such purpose. But in order to provide a reliable metric by which to evaluate hair loss and even the effect of treatment, the status of hair loss has to be determined at different times over the same geographic area.

The prior art systems, even those employing imaging systems, determine the status of hair loss that is difficult to compare at different time intervals because the area of interrogation is not well defined geographically. Generally the areas under interrogation are in the order of 10 to 50 square millimeters. Since the total area of scalp is 50,000 square millimeters, the need for accurately accounting for the geographical location of individual measurements that only covers 10 to 50 square millimeters is paramount.

The prior art incorporates relatively small static images over a relatively large area for analysis. The present invention is based on the recognition that a streaming video analysis can also be incorporated to provide more data points in the algorithm.

The present invention is based on the recognition that a metric for hair loss can be produced by imaging areas of any hair bearing skin which are sufficiently large (i.e. 50,000 square millimeters of the human scalp) that the focal areas can be later revisited reliable where any offset in positioning would introduce only acceptably small errors. A map of the hair bearing skin or scalp can be generated by a compilation of the images to provide a reliable metric of hair loss status for comparison with the metrics previously generated. The invention provides a method and apparatus for geographically mapping user defined locations of hair bearing skin area with a bulk metric output. The metric values may be used to compare different user defined locations to quantify relative differences by location. The metric values may also be used to compare user defined locations at different time intervals to quantify relative differences over a period of time. The mapping and the metrics can be achieved more specifically by automated means by the analysis of multiple static pictures or the analysis of a live video covering a larger area than a single, static field of view. It also provides a method and apparatus for sorting and characterizing the relative diameter of a hair shaft by automated means in which the total cross sectional area of all the hair shafts in the interrogated field can be calculated. The automated method of obtaining this metric can be effectively used to acquire the bulk of hair over user defined locations and time intervals.

Hair on the scalp that is susceptible to androgenic influence may exhibit a relative decrease in shaft diameter and number. This phenomenon is sometimes described as miniaturization of hair as is described above. Miniaturization of hair may also be due to various disease states as well as the natural life cycle of hairs. The present invention incorporates a device to interrogate an area of hair bearing scalp. The image(s) are digitized and processed by a pre-programmed algorithm to differentiate the hairs against its background. This differentiation is quantified by automated means to express a value of number of hairs per area and Density (D). Furthermore, the aforementioned image is processed by another pre-programmed algorithm to differentiate the differences in hair shaft diameter (or its thickness) within the image field(s). This differentiation is also quantified by automated means to express a value of Miniaturization (M).

For the purpose of simplicity in demonstrating aforementioned concept, the Density (D) may be expressed as a relative number that is the sum of the area that all the hair ($\Sigma H$) occupies in an image divided by the total area (A) of the image field ($D=\Sigma H/A$). The Miniaturization (M) may be expressed as a relative number that is the sum of the areas occupied by hairs with a smaller diameter ($\Sigma h$) divided by the sum of the area that all the hair (H) occupies in an image ($M=\Sigma h/\Sigma H$)

In effect, this automation produces metrics for Density (D) and Miniaturization (M). It also provides metrics for the bulk (B) of hair that is expressed as the total cross sectional area occupied by hair divided by the area under interrogation. This provides a quantifiable value in assessing the state of hair density, miniaturization, and bulk for the purpose of diagnosis. The variation of (M), (D), and (B) over different location and at different times will provide valuable information to the end user for the diagnosis and progression of hair loss or hair gain. The pattern of hair loss can also be determined with the aforementioned metrics. It is this ability to map out a metric based system for the status of hair loss at multiple locations sufficiently large to be accurately revisited and in a relatively short time window (seconds or minutes) that is the essence of this invention. When longer time intervals are used (weeks. months and years) an assessment of change in hair bulk can be measured. This method and apparatus would be particularly useful for documentation of hair loss or gain progression over time and/or hair gains in bulk after treatment regimens have had time to work. Drugs like finasteride (Propecia) are but one example of such a treatment regimen.

Another embodiment of the invention consists of a hand held device which a user moves from front to back along the scalp to establish a path of sufficient size to permit accurate measurements. The end user points the sensor end to the location of interest to obtain readings as the sensor is moved. The bulk of hair may be expressed in many ways depending on the aforementioned metrics and may incorporate the cross sectional area the hair shafts occupy in a field of interrogation. In this particular embodiment, a relative 'hair bulk' number may be expressed so that the end user can compare the value to the value at other locations or compare the value to other references on the individuals anatomy over time. This embodiment would conveniently have a recording and analysis function to keep track of the different data and reference points with dimensional locations mapped out. It could represent various static images or a 'video like' device that enables a person to sweep the hair bearing area along a series of tracks in a pattern that will, in effect, produce a more detailed map of hair bulk in the scalp, by area. In practice the device may be adapted to keep track of the velocity of movement and reference of a user defined location and record the time of data acquisition.

Another embodiment of the device utilized the same instrument without cutting the hairs to a small length. By using a combing device. The hair can be separated (parted) such that the scalp is exposed with hair on both sides, visualizing only the point where the hair exits the scalp before it is combed aside by the separating comb-like element. Standardization of the combing process is necessary in any one person and this can be accomplished by mechanical (comb) or pneumatic (air blowing) means.

Another embodiment of the device incorporates a miniaturized probe, like a ball point pen, which can be advanced over a section of scalp, separating the hairs as the probe moves through the 'forest' of hair shafts by mechanical or pneumatic (air blowing) means.

DESCRIPTION OF AN ILLUSTRATIVE EMBODIMENT OF THIS INVENTION

FIG. 1 is a schematic representation of a system embodiment of this invention showing the image capture apparatus;

FIGS. 2, 3, and 4 are schematic fields of view with the apparatus of FIG. 1 showing illustrative views of portions of the scalp or hair bearing skin;

FIG. 6 is a schematic view of a scalp or hair bearing skin with imaginary path and geography indicators as a reference for establishing grid indicia for location revisiting during sequential valuations; and FIG. 7 is a handheld embodiment in accordance with the principles of this invention.

DETAIL DESCRIPTION OF ILLUSTRATIVE EMBODIMENTS OF THIS INVENTION

Apparatus in accordance with the principles of this invention contains a digital recording device (camera), a computer that contains a contrast enhancing algorithm, housing for the camera type device or a device that acquires a digital signal through other means, and a computer that receives the digital output. A known surface area of hairy skin is imaged. The computer uses a contrast enhancing algorithm to maximally define and calculate the mass of the hair in the portion of skin under measurement. When the method is applied to an apparatus, the end result will be a bulk measurement of hair per unit area. If one area of the scalp is compared to another area of the scalp, different areas of the scalp may have similar or different measurements. If the measurement of hair bulk in one area is less than the hair bulk in another area, some disease or process may be present.

Measurements of hair bulk compared over a defined time period can establish metrics that will follow the progression of a disease that impacts hair bulk, or the value of treatment regimen for balding or thinning hair, particularly when a baseline area is established. Such a device can determine a decreasing mass of hair caused by reduced densities of the hair or reduced bulk of the hairs in a field(s) of view.

Figure 1:
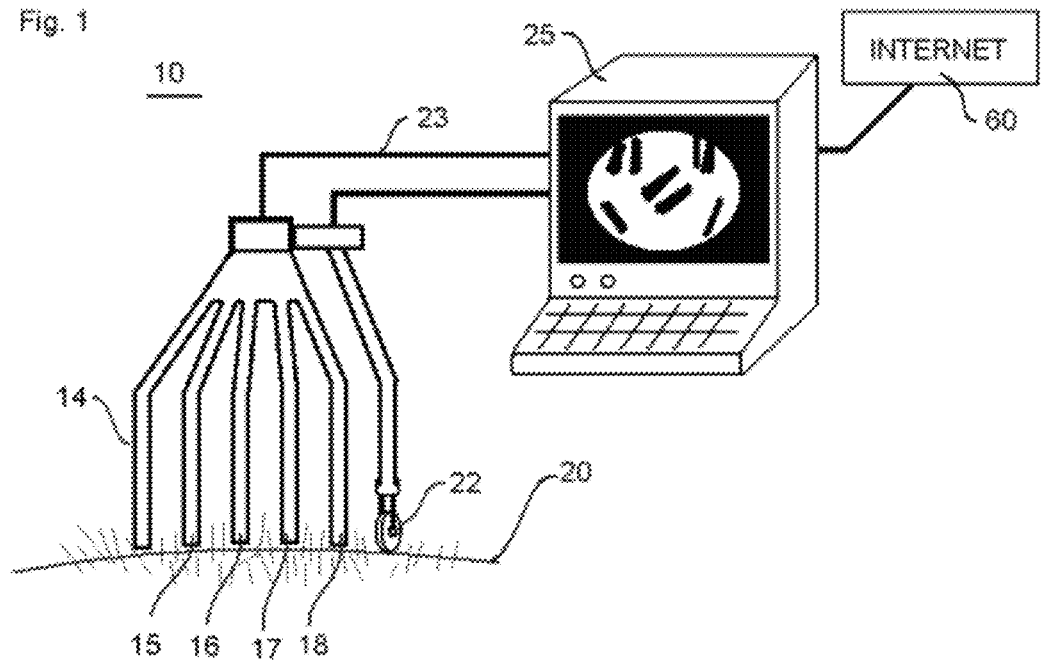

FIG. 1 shows a schematic representation of a system 10 for acquiring and processing a digital image of a scalp for determining the degree of hair loss in selected area of a scalp and the mapping of the entire scalp for providing a metric for reference by a health care professional. The figure shows an illustrative comb like structure 11 comprising a spine member 12 from which a number of tines (Illustratively five) 14, 15, 16, 17 and 18 extend. Tines 14, 15, 16, 17 and 18 are shown as having equal length and are intended for contacting a scalp 20 to facilitate the parting and or aligning of hairs. For the purpose of simplicity of concept this location tracking apparatus 22 shown in FIG. 1 is a small wheel that contacts scalp 20 that is in effect an odometer. In another embodiment the location tracking apparatus may be incorporated into a sensor wherein an incorporated velocity meter and accelerometer can calculate the relative distance traveled by said structure 12 may be calculated.

Each "tine" of comb-like apparatus 12 of FIG. 1 may comprise an optical device including imaging optical fiber(s) or a lens system to facilitate the interrogation of the imaging field of view 21. Sensor 20 may, for example, comprises a digital camera operative to transmit a digital data stream of the image of a field of view 21 of the scalp as show in figures.

The field of view 21 is determined by optical device or an imaging apparatus. The optical device may comprise a bundle of fibers and may be adapted for focus adjustment by, for example, adjusting the position of the fibers along its axis or by lens at the fiber tip and a MEM's apparatus for distorting the lens to adjust the focal plane. The field of view may be sufficiently illuminated by the ambient light in a surgical suite where the hair loss evaluation is conducted. However additional auxiliary lighting (not shown) can be provided by the apparatus in line with the optical device or image capture member.

The digital data stream of the captured image is transmitted via line 23 (or wirelessly) to computer processor represented at 25 in FIG. 1.

Figure 2:
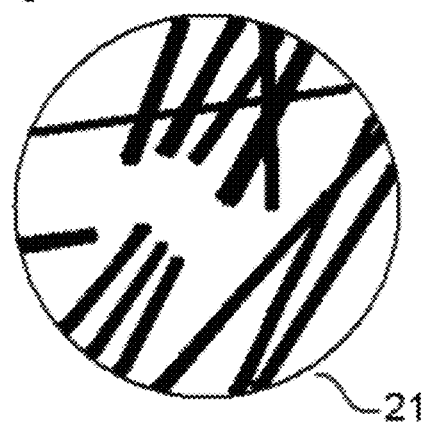

FIG. 2 represents an illustrative field of view showing a plurality of hairs a various angles and of varying thicknesses. The image capture member provides a data stream representative of image. Computer 25 stores the data stream and enhancement and end point analyses stored therein calculates the number of hairs in the field of view, the number of hairs having a cross sectional area less then a preset number, and uses this information to provide a valuation number for the hair loss in the field of view which is free of subjective evaluation by the operator.

Figure 3:
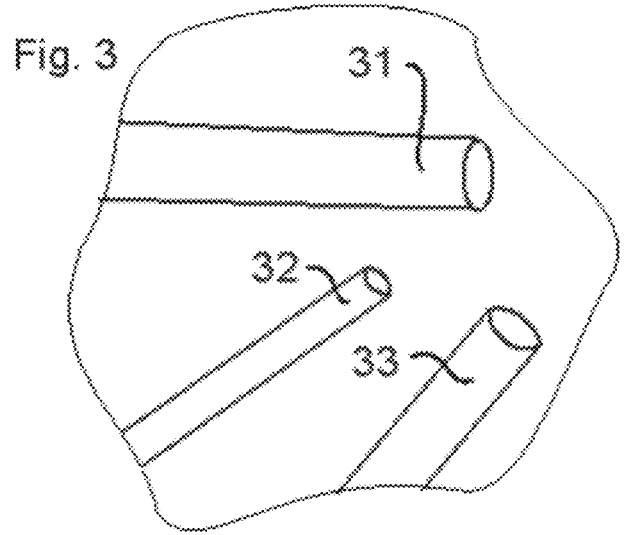

FIG. 3 illustrates several hairs which may be found in a field of view 21 of FIG. 1. Hairs 31 and 33 has a "large" cross sectional area with a diameter "D". Hair 32 has a small diameter ("d"), indicative of hair miniaturization. The thickness of the hairs may be determined by first identifying the location of the pores and the location of the edges of a hair associated with that particular pore. The algorithm may follow the hair shaft a short distance beyond the pore (i.e. 1 mm), determine the maximum gradient in intensity on the edge of the hair shaft which should be perpendicular to the hair shaft direction, and follow that gradient to the opposite edge, counting the number of pixels from one edge to the other to determine the hair diameter, D. The second stage of the algorithm then places hair into one of two bins, N or M. Bin N keeps track of the number of normal hairs and bin M keeps track of the number of miniaturized hairs. The normal hair diameter may be taken from the average diameter of a dense region of the scalp of a particular patient or from a population average which may be categorized by race, hair color, complexion, etc. Normal hairs are defined as hairs with a diameter between an adjustable lower cutoff value, b, and adjustable higher cutoff value, c. Miniaturized hairs are defined as hairs with a diameter between an adjustable lower cutoff value, 'a', and higher cutoff, 'b'. For every calculated hair diameter, if D<b, M is incremented by one. If D>b, N is incremented by one and the total hair count, T=N+M, the sum of the normal and miniaturized hairs. The output of the algorithm is thus, T and N/T where N/T is a number from 0% -100% depending on the degree of miniaturization in a particular region of the scalp. T is simply the hair count density. The cutoff value, b, will not necessarily be arbitrary but may be chosen based on the distribution function of individual hair diameters. In cases where the probability density function is a bimodal distribution, a good choice of b may be the minimum between the two peaks in the distribution.

Figure 4:
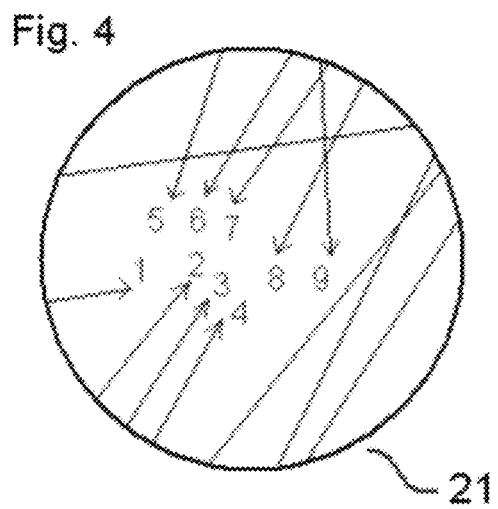

FIG. 4 shows the hairs in the field of view (21) which have end points (i.e. 1-9). Processor 25 includes software for end point determination which along with contrast enhancement software permits the requisite calculations herein to be made. End point contrast enhancement software is commercially available from vendors such as Adobe or Google, some of which are freely licensed for public use. Commercial software packages are currently available (TrichoScan by a Germany company Tricholog, and Folliscope by a Korean company Hairscience) to count and analyze hair diameter. The existing software offerings do not account for the hair bulk measurement and do not track measurement time intervals or geographically map the location of the measurements. Furthermore, the existing software offerings only analyses a static image and do not incorporate the analysis of a moving video image.

The edges of hairs in the image need to be identified using edge detection software such as Roberts Cross, Sobel, or Canny algorithms. One can simply take the mathematical derivative of an image to enhance the edges since a derivative will highlight the pixels where the intensity changes the most at the edge of most objects in the field of view. The coordinates of the edge pixels are located and entered into another algorithm which is capable of identifying objects. One example is a Hough Transform which sorts individual objects into classes determined by user defined parameters.

In order to identify individual hairs in the image, each object may be assigned an attribute class according to chain codes (Freeman, 1961). Chain codes map pixels along the edge of an object to simple codes related to the direction of the edge. By analyzing chain codes, simple shapes may be determined with a short series of numbers and similar objects will have similar chain codes in general. By following the edges of hairs within the image, individual objects within a field of view may fall into a number of different classes, (i.e.—hairs which completely cross the field of view, hairs which end at the base, hairs which end at the tip, crossing hairs, etc.) Hair shafts with pores will have a characteristic chain code since the edge will be changing direction very rapidly at the location of the pore. The location and number of pores with hairs can be counted and given the variable T which will be the total hair count.

Figure 5:
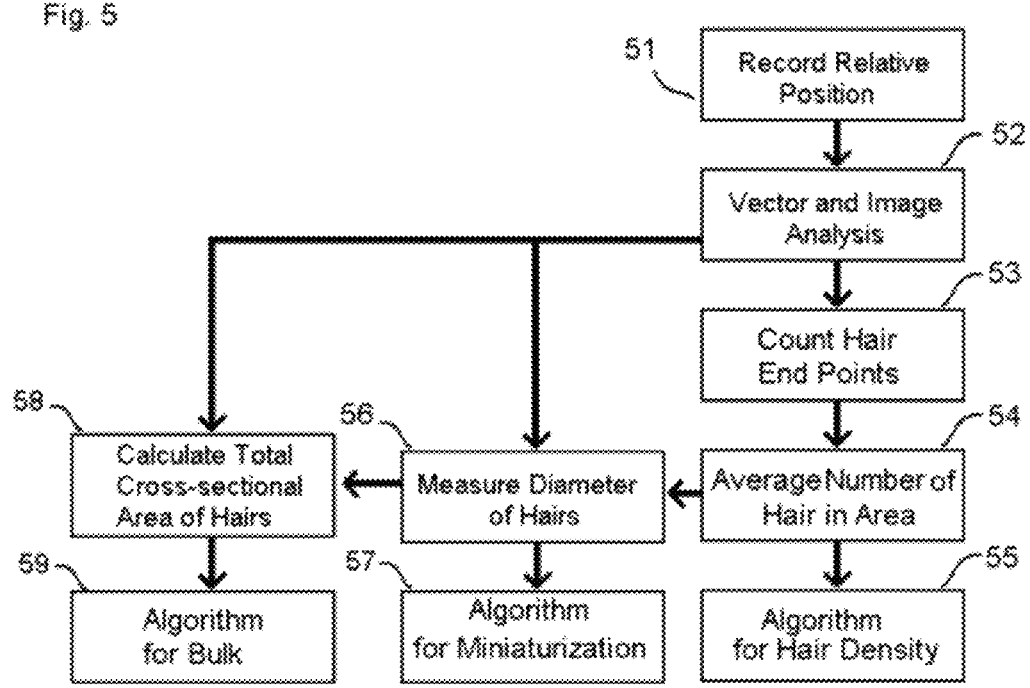
FIG. 5 is a flow diagram of the operation of the system of FIG. 1 responsive to field of view images of the type shown in FIGS. 2, 3, and 4.

FIG. 5 is a flow diagram of the operation of the processor on the digital data stream. The operation represents an analysis of the data collected by the apparatus of this patent. Initially the relative position of the apparatus of this patent is recorded as indicated in block 51. An image is acquired in the interrogation field as indicated in block 52 and hair end points are counted as indicated in block 53 (also see FIG. 4). Block 54 indicates the average of the sum of the hairs in the incremental areas. The hair density with respect to the recorded relative position of the apparatus of this invention is indicated in block 55. Block 55 represents the steps of finding the number of hairs in or incremental area of the field of view (typically less than 10 mm2) which for the typical Caucasian male has twenty hairs.

The diameter of hairs in the interrogation field are measured as indicated at block 56 and processor 25 calculates miniaturization and the number of hairs per area of the field of view as indicated at block 57.

The total cross-sectional area of hairs in field is calculated in block 58 to find the bulk of hairs indicated at block 59.

The comb-like structure 11 of FIG. 1 or 65 of FIG. 7 is moved over the scalp of a patient to acquire the image of successive fields of view to provide a comprehensive evaluation of the type of male baldness and the progress of hair loss. The relative position and the accounting of the location at which the aforementioned data are acquired is facilitated by a location tracking apparatus 22 or 64 of FIG. 1 or 7 respectively.

FIG. 6 shows a geographically mapped layout of the scalp with key reference locations marked in a grid for examination. The acquisition of successive image acquisitions and processing as described herein before provides complete metric for evaluation free of subjective variation.

The movement of the comb-like structure (12) or device (65) about the scalp of a patient is determined by the end user or by preprogrammed robotic manipulation of the structure (12 or 65). The positioning as well as the timing for acquiring each of successive data streams representative of a succession of fields of view may be by template registered on a patients scalp such as shown in FIG. 6 where the template may comprise a projection of the scalp.

Comb-like structure 12 or device 65 may be employed by an individual concerned about hair loss. In such a case, an individual with a computer may transmit image representing digital data streams over the internet to the office of a hair transplant surgeon for evaluation. Transmission via the internet is represented at 60 in FIG. 1.

The metric data 73 on one location and other metric data 74 on another location (see FIG. 6) can be stored in the device for comparative analysis between different location and different time intervals.

FIG. 7 shows another embodiment of the invention wherein a hand held device 65 is used against a hair bearing skin 62. In this embodiment, the device is a portable stand alone instrument that incorporates a sensor 63 that scans the hair bearing area of skin and outputs a relative metric display 61 associated with the bulk of hair, miniaturization, and density. The end user would point the sensor end 63 to the area of interest to obtain a reading 61. The bulk of hair may be expressed in many ways depending on the metric units and/or size or number of hairs or the cross sectional area the hair shafts that occupy in a field of interrogation. In this particular embodiment, a relative number is expressed so that the end user can compare the value to other areas of anatomy or compare the value to other references in time. This embodiment conveniently has a recording and analysis function to keep track of the different data and reference points based on a location tracking apparatus 64. For the purpose of simplicity of concept this location tracking apparatus 64 shown in FIG. 7 is a small wheel that is in effect an odometer. Another embodiment of the location tracking apparatus may be incorporated into the sensor 63 wherein a velocity meter and accelerometer can calculate the relative distance traveled by said hand held device 65.

Figure 8:
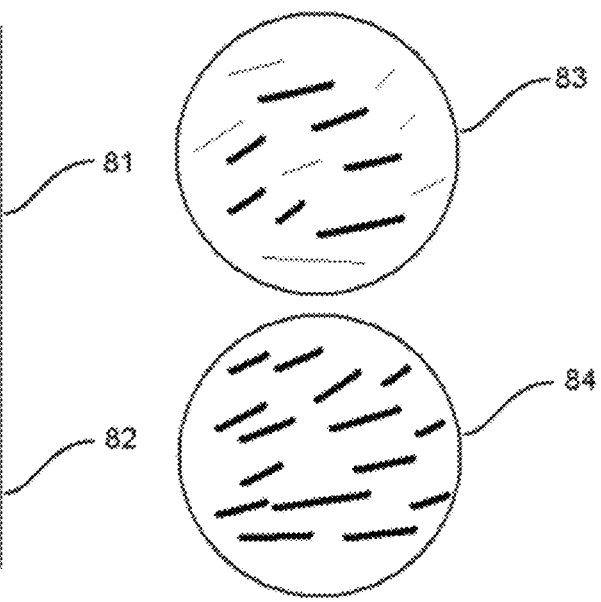
FIG. 8 shows an embodiment of the metric data representation between two time intervals.

FIG. 8 shows an embodiment of the metric data representation between two time intervals 81 and 82. The respective corresponding graphical representation is also shown in 83 and 84. A baseline metric 81 along with the graphical representation 83 is obtained from a geographic location such as 73 in FIG. 6. This same geographic location is again interrogated at another time and a new metric 82 along with the graphical representation 84 is represented with the relative change from the prior metric 81. The metrics should be sampled a few times (3 to 4 times) on the localized (50 to 500 square millimeters) area of interest so that an average value of the local area can be reliably sampled. Aside from such sampling, a video stream may obviate the need of multiple static image sampling as it continually samples the images in the area of interest.

What has been described is merely illustrative of the principles of this invention. It is to be understood that it is within the preview of those skilled in the art to make various modifications thereof still within the scope of the invention or encompassed by the following claims:

What is claimed is:

1. A method for determining a value of the degree of hair loss over a hair bearing area, using a digital imaging apparatus and a specially programmed processor for digital image processing to determine quantification and qualification output data and for algorithms for calculations using the output data, said method comprising the steps of obtaining a digital image of each of a sequence of fields of view corresponding to segments of a path or geographical area, said field of view having an area sufficient to permit revisiting said path or geographical area with only negligible averaging error relative to data available, generating an integrated digital data stream representative of the entire path or geographical area, manipulating the data stream to determine: 1) the number of hairs in said path or geographical area, 2) the diameter of each of said hairs, and 3) the sum of the cross sectional areas of said hair.

2. A method as in claim 1 including the steps of determining the sum of the number of hairs in each of a first group and a second group of hairs, said first group comprising hairs with diameters or width smaller than a predetermined value taken from a reference site elsewhere on the scalp, said second group comprising hairs with diameter or width larger than a predetermined value taken from the same reference site elsewhere on the scalp and applying an algorithm, dividing the sum of the number of hairs in said first group by the sum of the number of hairs in both said first and second groups.

3. A method as in claim 1 further comprising establishing a defined location of the sequence of fields of view and after a predetermined time revisiting the defined location and repeating the steps and comparing the results.

4. The method of claim 1 further comprising:
 after passage of a selected time, repeating the steps and comparing the results.

5. A method for determining a value of at least one metric that is indicative of hair loss over a hair bearing area, using a digital imaging apparatus and a specially programmed processor said method comprising the steps of:
 selecting a path or geographical area to be examined for hair loss;
 obtaining a digital image of each of a sequence of fields of view corresponding to segments of the path or geographical area, said field of view having an area sufficient to permit revisiting said path with only negligible averaging error,
 generating an integrated digital data stream representative of the image of said entire path or geographical area;
 digitally processing the digital data stream for extracting digital measurement data of selected hair quality and/or quantity data;
 using the extracted digital measurement data algorithmically determining a value of at least one selected metric according to an applicable algorithm or algorithms:
 providing a sensible output or recordation of the value of the at least one metric.

6. The method of claim 5 wherein the field of view is at least about one square centimeter.

7. The method of claim 5 wherein the at least one metric is selected from the group consisting of:
 bulk (B),
 hair diameter (D),
 total hair count (T)
 normal hair count (N) and miniaturized hair count (M)
 hair density and
 a combination bulk normal hair count and miniaturized hair count.

8. The method of claim 5 further comprising:
 after passage of a selected time, repeating determination of the value of the at least one metric.

\* \* \* \* \*